United States Patent
Baets et al.

(10) Patent No.: US 9,770,196 B2
(45) Date of Patent: Sep. 26, 2017

(54) SENSING OF COMPONENTS IN LIQUIDS

(71) Applicant: UNIVERSITEIT GENT, Ghent (BE)

(72) Inventors: Roeland Baets, Deinze (BE); Eva Ryckeboer, Ghent (BE)

(73) Assignees: UNIVERSITEIT GENT, Ghent (BE); IMEC VZW, Leuven (BE)

(*) Notice: Subject to any disclaimer, the term of this patent is extended or adjusted under 35 U.S.C. 154(b) by 226 days.

(21) Appl. No.: 14/091,645

(22) Filed: Nov. 27, 2013

(65) Prior Publication Data
US 2015/0148627 A1 May 28, 2015

(51) Int. Cl.
| | |
|---|---|
| A61B 5/145 | (2006.01) |
| A61B 5/1459 | (2006.01) |
| G01N 21/03 | (2006.01) |
| G01N 21/27 | (2006.01) |
| A61B 5/15 | (2006.01) |
| A61B 5/157 | (2006.01) |
| B01L 3/00 | (2006.01) |

(52) U.S. Cl.
CPC ........ *A61B 5/14532* (2013.01); *A61B 5/1459* (2013.01); *A61B 5/157* (2013.01); *A61B 5/150022* (2013.01); *G01N 21/03* (2013.01); *G01N 21/274* (2013.01); *A61B 5/14503* (2013.01); *A61B 2562/04* (2013.01); *B01L 3/5027* (2013.01); *G01N 2201/0662* (2013.01)

(58) Field of Classification Search
CPC ....... A61B 5/0205; A61B 5/0215; A61B 5/05; A61B 5/145; A61B 5/14503; A61B 5/14532; A61B 5/1459; A61B 5/1495; A61B 5/1455; A61B 5/14546
See application file for complete search history.

(56) References Cited

U.S. PATENT DOCUMENTS

| | | | | |
|---|---|---|---|---|
| 5,251,007 A | * | 10/1993 | Rinke ............ | G01J 3/2803 356/319 |
| 6,049,727 A | | 4/2000 | Crothall | |
| 6,361,206 B1 | * | 3/2002 | Bonne ............ | G01F 1/6842 374/135 |
| 2002/0041827 A1 | * | 4/2002 | Yager ............ | G01N 30/0005 422/400 |
| 2002/0049389 A1 | * | 4/2002 | Abreu ............ | A61B 3/1241 600/558 |

(Continued)

OTHER PUBLICATIONS

Ryckeboer et al., "Measurement of small molecule diffusion with an optofluidic silicon chip", Lab Chip, 2013, 13, 4392-4399.*

*Primary Examiner* — Eric Winakur
*Assistant Examiner* — Chu Chuan (JJ) Liu
(74) *Attorney, Agent, or Firm* — Workman Nydegger (57) ABSTRACT

A sensing system and method for sensing a component in a liquid is disclosed. The system comprises a microfluidic channel, the microfluidic channel comprising a first end and a second end, wherein the microfluidic channel is open at the first end and closed at the second end. The system also comprises at least one measurement sensor positioned adjacent the first end, the measurement sensor being arranged for detecting a measurement signal and a reference sensor positioned in the microfluidic channel adjacent the second end, the reference sensor being arranged for detecting a reference signal of the liquid. The system further is configured for combining the measurement signal and the reference signal so as to filter out background influences.

20 Claims, 7 Drawing Sheets

(56) References Cited

U.S. PATENT DOCUMENTS

2003/0032892 A1* 2/2003 Erlach .................. A61B 5/0031
 600/547
2009/0123961 A1* 5/2009 Meyvantsson ...... B01F 13/0059
 435/29
2011/0218490 A1* 9/2011 Ocvirk ............... A61B 5/14532
 604/66
2011/0294154 A1* 12/2011 Jaron ................. G01N 33/5302
 435/29
2013/0296174 A1* 11/2013 Peumans ............... B01L 3/5027
 506/2

* cited by examiner

SENSING OF COMPONENTS IN LIQUIDS

FIELD OF THE INVENTION

The invention relates to the field of sensing and/or quantifying components in a sample. More specifically it relates to a system and method for detecting or sensing, optionally quantifying, a component in a sample, using a reference signal.

BACKGROUND OF THE INVENTION

Accurate detection and/or quantification of components in liquids is used in a plurality of applications. The accuracy of detection and/or quantification is not only dependent on the quality of the sensor by which the component is sensed, but typically also requires compensating for background and/or environmental effects that are present during the detection process. Such background and/or environmental effects may include a variety of effects such as for example drifts in sensing elements, temperature effects, other environmental effects, the presence and/or absence of other components in the liquid to be characterized, slow shifts in the composition of the liquid to be characterized.

A plurality of techniques for generating a reference signal is known. The most commonly known technique is the recording of a reference signal using a blank measurement. When performing a blank measurement, typically a measurement is performed with a reference sample or without a sample being present. This reference signal is then used for compensating the measured sensor used for characterizing. A disadvantage of using a blank measurement is that it typically is pre-recorded, thus not guaranteeing the same conditions as those present during the measurement. Using a blank measurement does typically not allow to bring into account effects on or by components of the liquid which do not need to be characterized, but certainly are necessary to take into account for accurate correction.

Another well-known principle to enhance the signal-to-noise of a set-up is to work 'dual-beam'. This means that a signal arm is created that is in contact with the substance that you want to sense and an identical reference arm is created that feels the same environment except for the substance that should be detected. By taking the ratio of the signal and reference measurements, the influence of the substance is revealed. This can be explained by the fact that all the common variations, caused by fluctuations in e.g. temperature, pressure, absorption etc. cancel out. Nevertheless, it is not easy to provide a proper reference sample.

One particular example is shown in U.S. Pat. No. 6,049,727, where an implantable sensor is presented. The sensor is developed for in vivo measurement of the spectra of body fluids. Light is emitted at a plurality of wavelengths and the absorption is determined after the light passes through the fluid. To compensate for drift of the laser diodes a portion of the output of the laser diodes is diverted to a calibration detector. This calibration allows to compensate for drift of the laser diodes, it however does not allow to compensate for changes in the medium through which the light is passing or any other environmental conditions influencing the system behavior.

Therefore there is still room for improvement in systems and methods for liquid characterisation.

SUMMARY OF THE INVENTION

It is an object of embodiments of the present invention to provide accurate systems and methods for sensing components in a liquid. It is an advantage of embodiments of the present invention that background changes inherent to the sensing technique as well as background contributions by elements not of interest in the liquid, background influences by temperature effects, etc. can be removed accurately from the measurement signal so that an accurate detection and optionally quantification is possible.

In embodiments of the present invention, use is made of the fact that a half closed microfluidic channel acts as a long diffusion path for the component to be sensed or identified, resulting in rapid variations of presence or in concentration in the liquid being averaged in the signal measured in the reference signal. In terms of diffusion, the reference sensor typically is placed far from the open end of the half closed microfluidic channel and the solute can only reach the reference sensor through the process of diffusion in a confined region.

It is an advantage of embodiments of the present invention that the process of diffusion will smooth all fast variations of the solute concentration that are present at the source. The reference sensor may be positioned in some embodiments at such a position that only a slowly varying solute concentration remains at the reference sensor.

Embodiments of the present invention may especially be suitable for detecting fast changes in the presence or concentration of a component of interest in a liquid. One example of an application that can be targeted using the present invention is glucose sensing, although embodiments of the present invention are not limited thereto. Other examples are detection of lactate, urea, proteins, small molecules, biomarkers etc. In one example, sensing may be sensing of an organic or inorganic solute in a liquid.

It is an advantage of embodiments of the present invention that a sensing system can be provided for continuous monitoring, e.g. the system does not need to be stopped for recording a blank measurement. Furthermore, such continuous monitoring can be performed using a reference signal that is representative of an up-to-date reference, i.e. taking into account background and/or environmental effects at the moments the measurements are made and not recorded at a significant other moment in time.

The above objective is accomplished by a method and device according to the present invention.

The present invention relates to a sensing system for sensing a component in a liquid, the system comprising a microfluidic channel, the microfluidic channel comprising a first end and a second end, wherein the microfluidic channel is open at the first end and closed at the second end, at least one measurement sensor positioned adjacent the first end, the measurement sensor being arranged for detecting a measurement signal, a reference sensor positioned in the microfluidic channel adjacent the second end, the reference sensor being arranged for detecting a reference signal of the liquid. The system further is being configured for combining the measurement signal and the reference signal so as to filter out background influences. It is an advantage of embodiments of the present invention that the reference signal used is not a mere blank, but is based on the same liquid as the liquid to be characterized, such that a more accurate reference signal is obtained.

The measurement sensor may be positioned in the microfluidic channel adjacent the first end. It is an advantage of embodiments of the present invention that the sensing system can be compact and can be configured such that everything is positioned in a single microfluidic channel. Alternatively, the measurement sensor also may be positioned outside the microfluidic channel, but still adjacent the first end thereof, and a reference signal generating system comprising the microfluidic channel and the reference sensor near the closed end may be combined therewith.

The measurement sensor and the reference sensor may be any suitable sensor such as for example an absorption sensor, a chemical sensor, an electrical sensor, a mechanical sensor e.g. a MEMS sensor or an optical sensor. It is an advantage of embodiments of the present invention that the sensing system can be based on any type of sensors, such that the best suitable sensor can be selected for sensing or quantifying the component in the liquid.

The measurement sensor and the reference sensor may be based on a transmitter/receiver architecture wherein the transmitter of the measurement sensor is shared with the transmitter of the reference sensor. It is an advantage of embodiments of the present invention that changes in the output power of the transmitter are detected in common in the measurement sensor and the reference sensor such that changes in the output power of the transmitter can be filtered out by comparing the measurement signal and the reference signal because both signals comprise the variations, e.g. the drift, of the transmitter.

The measurement sensor and the reference sensor may be optical sensors using a common excitation source as transmitter. It is an advantage of embodiments of the present invention that variations in the excitation source are also automatically compensated for and that consequently, these variations do not influence the measured data.

The measurement sensor and the reference sensor may be part of a dual beam optical sensor system. It is an advantage of embodiments of the present invention that these may make use of known principles for dual beam optical sensing. In the present invention, such principles are combined with the principle of using a closed end microfluidic channel and diffusion therein for creating a suitable reference.

The measurement sensor and the reference sensor may be spectral optical sensors allowing spectral characterisation of the fluid. It is an advantage of embodiments of the present invention that spectral sensors can be used as these allow accurate detection and optionally also quantification of components in the liquid.

The measurement sensor and the reference sensor may be optical sensors based on a resonator element. It is an advantage of embodiments of the present invention that accurate results can be obtained. The resonator element may be an optical resonator ring.

The measurement sensor may comprise a spectral optical sensor and the reference sensor may comprise a second spectral optical sensor and the first spectral optical sensor may be in contact with the liquid at the open end and the second spectral optical sensor may be in contact with the liquid at the closed end. In one embodiment, the measurement sensor may comprise a first optical ring and the reference sensor may comprise a second optical ring and the first optical ring may be in contact with the liquid at the open end and the second optical ring may be in contact with the liquid at the closed end. In one embodiment, the spectral optical sensor(s) may comprise a long waveguide, e.g. wrapped up in a spiral shape. It is an advantage of embodiments of the present invention that changes in the liquid in contact with the spectral optical sensor, e.g. the presence of a component in the liquid or a change in concentration of the component in the liquid, will cause a change in the transmission characteristic of the spectral optical sensor. Where in embodiments of the present invention reference is made to a spectral optical sensor reference is made to a sensor using an optical signal comprising spectral information for sensing. Such a sensor thus typically may comprise a region where interaction between the radiation and the sample to be analysed occurs. Such region may for example be established in an optical ring or in a long waveguide, e.g. wounded as a spiral.

The microfluidic channel may have a length that is at least such that the time needed for the analyte molecules to diffuse from one end to the other is large as compared to the time over which the analyte undergoes relevant concentration changes in the given application. In a particular example, the length may be 2 times the diffusion speed over time for the component targeted with the sensor, advantageously at least 5 times the diffusion speed over time for the component targeted, more advantageously at least 10 times the diffusion speed over time for the component targeted. The length may be selected such that the diffusion coefficient of the component targeted and the average time required for ensuring that extreme changes in concentration at the open end result in negligible changes at the closed end. For a small molecule such as glucose for example, a length of e.g. 1 cm could be used. It is and advantage of embodiments of the current invention that the length of the microfluidic channel is so long that the concentration changes of the component(s) under study at the open end are averaged out so that these are not noticeable or significantly reduced at the closed end.

The microfluidic channel may comprise a diffusion barrier for a component to be detected. It is an advantage of embodiments according to the present invention that the length of the microfluidic channel can be shortened if other diffusion barriers are used.

The microfluidic channel may have a curved shape such that the first end of the channel is nearby the second end of the channel. It is an advantage of embodiments according to the present invention that the measurement and reference sensor are positioned close to each other so that variation on the environmental effects that are filtered out by the reference sensor, e.g. temperature, can be as small as possible. It thus can be advantageous that both ends are in close proximity to each other.

The measurement sensor and the reference sensor may be configured for directly combining the signals for compensating the measured signal with the reference signal. It is an advantage of embodiments according to the present invention that compensation can be provided even before the measured signals are converted into digital or electrical data signals.

The sensing system may comprise a processor for receiving the measurement signal of the measurement sensor and the reference signal and for combining the reference signal with the measurement signal for eliminating the common sources of noise. Combining may comprise dividing and/or subtracting of the signals. It is an advantage of some embodiments of the present invention that combining signals can also be performed in the processor by data processing and does not need to be implemented at hardware level in the sensing part itself.

The sensing system may be an implantable sensor for implantation into a living creature. It is an advantage of some embodiments of the present invention that an accurate glucose sensor can be obtained that can be implanted in a human or animal body.

The present invention furthermore relates to a method for sensing a component in a liquid, the method comprising obtaining a measurement signal of a fluid to be characterized using a measurement sensor adjacent a first, open end of a microfluidic channel, obtaining a reference signal for the fluid to be characterized using a reference sensor adjacent a second, closed end of the microfluidic channel, and compensating the measurement signal with the reference signal so as to filter out background influences. The method furthermore may comprise steps corresponding with the functionality of components and/or features of the system as described above.

The present invention also relates to the use of a sensor as described above, for quantification of a glucose level in a living creature.

It is an advantage of embodiments of the present invention that the sensing system, including the reference signal generating system, can be made small, allowing optionally good biocompatible packaging. The sensor may be substantially flat. Such good biocompatible packaging may reduce or minimize bio-fouling.

It is an advantage of embodiments of the present invention that the sensing system can have substantially direct access to the substance or sample under study. It is an advantage of embodiments of the present invention that the sensing system can assist in providing a closed loop drug delivery system, such as a closed-loop insulin delivery system that is implantable in a patient's body. Sensing systems according to embodiments of the present invention therefore may be coupled to a drug delivery system and may provide an output signal to the drug delivery system.

It is an advantage of embodiments according to the present invention that it can assist in non-invasive—after implantation—measurements e.g. glucose or urea measurements, allowing high frequency tests without patient discomfort. The reference measurements thereby stay up to date automatically.

Particular and preferred aspects of the invention are set out in the accompanying independent and dependent claims. Features from the dependent claims may be combined with features of the independent claims and with features of other dependent claims as appropriate and not merely as explicitly set out in the claims.

These and other aspects of the invention will be apparent from and elucidated with reference to the embodiment(s) described hereinafter.

The drawings are only schematic and are non-limiting. In the drawings, the size of some of the elements may be exaggerated and not drawn on scale for illustrative purposes.

Any reference signs in the claims shall not be construed as limiting the scope.

In the different drawings, the same reference signs refer to the same or analogous elements.

DETAILED DESCRIPTION OF ILLUSTRATIVE EMBODIMENTS

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice of the invention.

Furthermore, the terms first, second and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

In the description provided herein, numerous specific details are set forth. However, it is understood that embodiments of the invention may be practiced without these specific details. In other instances, well-known methods, structures and techniques have not been shown in detail in order not to obscure an understanding of this description.

Where in embodiments of the present invention reference is made to "the characteristic of a liquid", reference is made to the presence and/or the concentration and/or the amount and/or the specific properties of a component under study. This can for example be the glucose level in a liquid, or the oxygen level in a liquid, or the concentration of any other material within a liquid.

Where in embodiments of the present invention reference is made to "the measurement signal", reference is made to the signal measured at the first end of the channel. The first end thereby typically is the open entrance end of the half-open microfluidic channel used in embodiments of the present invention. The measurement signal comprises the effect directly coming from the presence of the component under study as well as any other background changes.

Where in embodiments of the present invention reference is made to "the reference signal", reference is made to the signal measured at the second end of the channel, which typically is the closed end of the half-open microfluidic channel. The measured reference signal comprises the background changes that are also occurring in the measurement signal and that need to be filtered out. By the provision of a microfluidic channel wherein the diffusion length, created by the length of the microfluidic channel or by introducing additional diffusion barriers, is long, the faster variations in presence, concentration or amount, of the component are averaged out and are not present in the reference signal.

Where in embodiments of the current invention reference is made to "the calibrated effect", reference is made to a signal which is the result of processing the measurement signal and the reference signal to eliminate background contributions in the measurement signal.

In a first aspect, the present invention relates to a sensing system for sensing a component in a liquid. Sensing a component may comprise detecting a presence of the component, sensing a concentration or concentration variation, etc. The system according to embodiments of the present invention is especially suitable for detecting fast varying component contributions, such as for example as typically occurring in a glucose level for a patient having diabetes. Nevertheless, embodiments are not limited thereto. Some other examples—also not limiting—include urea, lactate, ceatinine, triglyceride, protein, cholesterol, ethanol, etc.

Embodiments of the present invention may be especially suitable—but not limited to—systems for sensing of a substance in the body of living creatures including the human being. The living creature may be any organism for which a sample containing a target substance can be obtained. It may for example be an animal, such as a mammal or non-mammal. It may be cold-blooded or warm-blooded.

According to embodiments of the present invention, the system comprises a microfluidic channel comprising a first end and a second end, wherein the microfluidic channel is open at the first end and closed at the second end. In other words, a half-open microfluidic channel is provided, being open at one end, but closed at all other sides, including at the other end. The system furthermore comprises at least one measurement sensor positioned adjacent the first end, the measurement sensor being arranged for detecting a measurement signal. The system also comprises a reference sensor positioned in the microfluidic channel adjacent the second end, the reference sensor being arranged for detecting a reference signal of the liquid. The system furthermore is configured or arranged for combining the measurement signal and the reference signal so as to filter out background influences. The latter can be obtained by arranging the sensors such that the signals obtained can be directly combined, in a hardware component, so that the reference signal is used for compensating. Alternatively the obtained signals can be provided as data to a data processor and can be processed in the processor such that the data corresponding with the reference signal are used for compensating.

Figure 1:
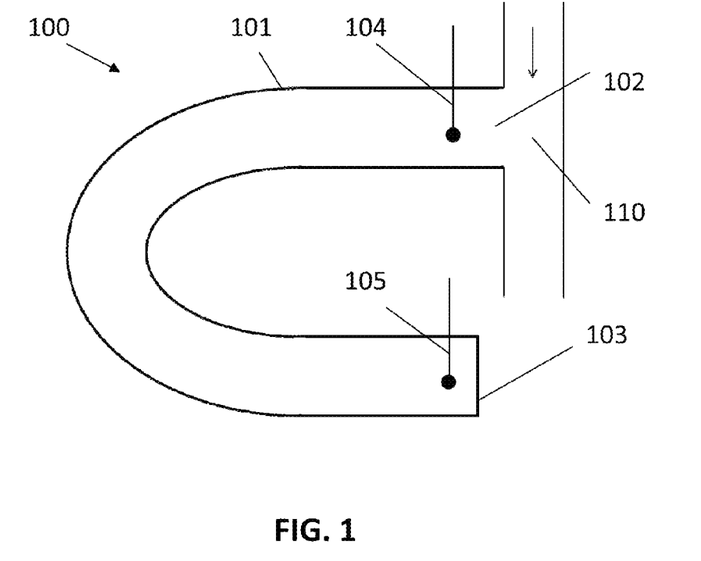
FIG. 1 provides a schematic view of a system for measuring the concentration of a component in a liquid in accordance with embodiments of the present invention.

By way of illustration, standard and optional features and advantages of embodiments of the present invention will be further discussed and illustrated with reference to the drawings. FIG. 1 illustrates a sensing system 100 for measuring the concentration of a component in a liquid. The system comprises a microfluidic channel 101. A first end 102 of the channel 101 is open and a second end 103 of the channel 101 is closed. The first end 102 is also called the open end 102. The second end 103 is also called the closed end 103. When in operation, the open end 102 is in contact with a liquid volume 110—which typically is not part of the sensing system—of the liquid to be characterised and/or monitored. The liquid volume 110 might be a stream, it might be enclosed by a vessel, or another channel. The liquid volume may be captured in a channel in direct contact with the microfluidic channel 101. Nevertheless, the microfluidic channel 101 might also be directly implanted in a living creature, without there being an additional channel present for the sensing system. Typically, in order to be sure that the open end 102 of the microfluidic channel 101 remains open during the operation lifetime of the system 100, precautions may be taken, e.g. by providing a filter element. The microfluidic channel 101 is at the open end 102 in contact with the environment, it might for example be directly placed in a liquid volume 110. At the open end 102 of the channel 101 the concentration of the component under study corresponds with the concentration of the component under study in the liquid 110 passing by the open end. In embodiments of the present invention, the microfluidic channel 101 may be an elongated microfluidic channel containing a fluid or hydrogel. A long microfluidic channel may have a length that is at least such that the time needed for the analyte molecules to diffuse from one end to the other is large as compared to the time over which the analyte undergoes relevant concentration changes in the given application. In a particular example, the length may be 2 times the diffusion speed over time for the component targeted with the sensor, advantageously at least 5 times the diffusion speed over time for the component targeted, more advantageously at least 10 times the diffusion speed over time for the component targeted. The length may thus be application dependent but typically may be in the order of centimeter. The channel may be rectangular in cross-section. It may for example have a height in the range 10 to 100 µm, e.g. 50 µm and a width matching the sensor size, advantageously smaller than 700 µm. In embodiments of the present invention the presence and/or concentration of a specific component or the presence and/or concentrations of multiple components in the liquid may be determined.

In embodiments of the present invention, the presence and/or concentration of the component typically is determined at the open end 102, while the reference signal to be used for compensating for background and/or environmental effects is recorded at the closed end 103. Advantageously, the concentration or presence of the component of interest changes much faster at the open end 102 of the channel 101 than the time it takes for the component to diffuse to the closed end 103 of the channel 101, resulting in that, due to the diffusion, the variation is averaged out at the closed end. The closed end 103 is therefore suited for obtaining a reference measurement. Nevertheless, the liquid at the closed end 103 is in direct contact with the liquid at the open end 102 and therefore has the same temperature, the same pressure and the same slow diffusing characteristics. The differences sensed in the liquid characteristics between the open end 102 and the closed end 103 therefore typically are only the fast changing liquid characteristics at the open end. In this perspective fast changing characteristics need to be compared to the time it takes for the components, related to the specific components under study, to diffuse to the closed end. The diffusion time is so long that the fast concentration changes are not present at the closed end 103. Merely an average of the concentration changes at the open end 102 will be measurable at the closed end 103. In one example, the length of the diffusion channel is determined as follows: Let the fastest concentration variation that is allowed have a frequency fmax, then one can calculate for every distance along the microfluidic channel by how much the signal at this frequency fmax is attenuated. If the detector has a dynamic range of e.g. 30 dB, the transfer function graph for the microfluidic channel length and molecular diffusion coefficient of the component targeted can show you at which location in the microfluidic channel the signal with a frequency fmax is damped by 30 dB and hence can no longer be detected.

The technique for compensating may be especially advantageous for small components, like for example glucose, since they cannot be filtered using a conventional filter.

In embodiments of the present invention the system 100 comprises a measurement sensor 104 at the open end 102, and a reference sensor 105 at the closed end 103. By placing the measurement sensor 104 at the open end 102 it will detect the variations in the concentration of components for which it is sensitive. In exemplary embodiments of the present invention the measurement sensor 104 is sensitive for variations in component concentration. The measurement sensor 104 may be any type of sensor suitable for detecting a characteristic of a component in the liquid, such as for example an electrical sensor, an absorption sensor, a chemical sensor, an optical sensor, etc. The measurement sensor 104 may for example be an optical sensor sensitive for absorption of a signal by the components. The reference sensor 105 may in principle be any sensor that allows to detect the background and/or environmental influences. Advantageously, as the effects are best comparable and most alike, the reference sensor 105 is of the same type as the measurement sensor 104.

Figure 2:
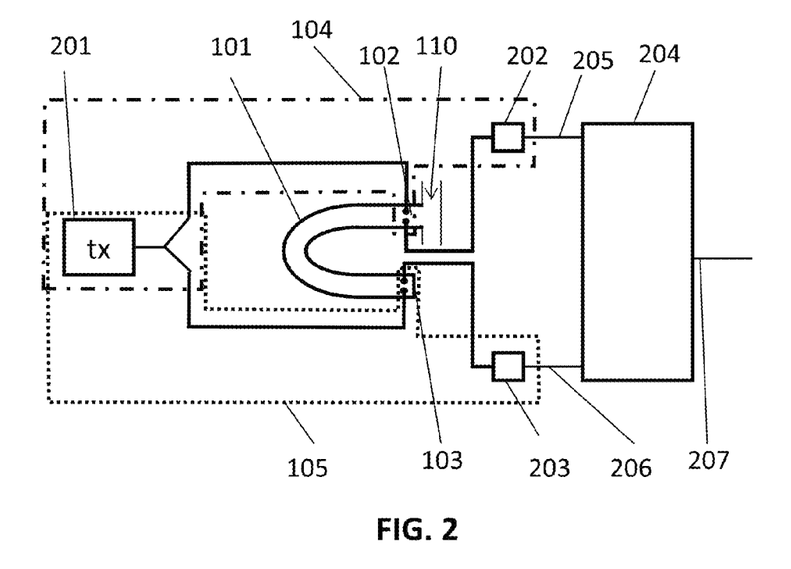
FIG. 2 provides a schematic view of an exemplary embodiment in accordance with the present invention.

In some embodiments of the present invention the measurement sensor 104 and the reference sensor 105 comprise a transmitter 201 and receiver 202, 203. In embodiments of the current invention one transmitter 201 is used for both the measurement sensor 104 and the reference sensor 105. By doing so variations in the transmit power of the transmitter can be calibrated out. In embodiments of the present invention, the sensors may be optical sensors and the transmitters may be one and the same optical radiation source, used simultaneously.

In this way, variation in the optical radiation source can be compensated for.

The exemplary embodiment shown schematically in FIG. 2, comprises, by way of example, a diffusion channel 101, a first, measurement sensor 104 at the open end 102 of the channel and a second, reference sensor 105 at the closed end 103 of the channel. Not limiting thereto the sensor might be an optical sensor, a RF sensor, or a chemical sensor. In the exemplary embodiment the first sensor 104 comprises a transmitting 201 and receiving part 202. Also the second sensor 105 comprises a transmitting 201 and receiving part 203. The transmitting part 201 is in the exemplary embodiment shared between both sensors such that the transmitted signal is identical for both sensors. In embodiments of the present invention, the transmitted signal might be an optical signal or an RF signal. In embodiments of the present invention, a first receiver 202 converts the measurement signal 205 from an analog signal to a digital signal and a second receiver 203 converts the reference signal 206 from an analog signal to a digital signal. In the exemplary embodiment illustrated in FIG. 2 a parallel setup of a first receiver 202 and a second receiver 203 is shown. In other embodiments of the present invention this might be one receiver sampling the reference signal and the measurement signal sequentially. In the exemplary embodiment illustrated in FIG. 2 a comparator 204 compares and/or processes the measurement signal 205 and the reference signal 206 and outputs a calibrated effect 207. Thereby the common signal present in both the measurement signal 205 and the reference signal 206 is removed from the measurement signal 205 resulting in the calibrated effect 207.

In embodiments of the present invention the reference sensor 105, positioned at the closed end 103 of the microfluidic channel 101, thus is used as a reference-arm. The reference signal 206 obtained by the reference sensor may for example be used to calibrate out drift. This drift might be caused by changes in the liquid (e.g. temperature changes) or changes in the transmit power.

By way of illustration, embodiments of the present invention not being limited thereto, a number of particular embodiments will now further be described.

According to a particular embodiment of the present invention, the measurement sensor 104, and the reference sensor 105 can be used in a spectrometer configuration. The spectrum thereby ranges between 1100 nm and 3500 nm or parts thereof, preferably between 1540 nm and 1610 nm. Also measurements at one or more fixed wavelengths are possible.

According to another particular embodiment, the measurement sensor 104 and the reference sensor 105 may be optical sensors implemented on a photonic chip. In embodiments of the present invention the measurement sensor 104 and the reference sensor 105 in the waveguide layer are in contact with the sample under test. In one example the measurement sensor and reference sensor comprise optical rings. The transmission characteristic of such optical rings is dependent on the liquid in contact with the waveguide layer of the optical ring. For example a concentration change of glucose in the liquid typically has an impact on the transmission characteristic of the optical ring. In embodiments of the present invention, compensating can be done by dividing the measurement signal 205 with the reference signal 206. In embodiments of the present invention this allows to eliminate background effects like for example temperature changes or changes in the power of the transmitter. The system 100 is build such that the background changes at the open end 102 are similar to the background changes at the closed end.

The reference signal 206 is again measured by the reference sensor 105 at the closed end 103 of the channel 101. The second sensor 105 does not pick up concentration changes of the component under study because the concentration changes of the component at the first open end 102 are significantly faster than the diffusion to the second closed end 103.

It is an advantage of particular embodiments of the present invention that these can be implemented as photonics integrated circuits. This refers to a variety of forms and material systems such as for example low-index contrast waveguide platforms (e.g. polymer waveguides, glass/silica waveguides, $Al_xGa_{1-x}As$ waveguides, $In_xGa_{1-x}As_yP_{1-y}$ waveguides), high-index contrast waveguides (e.g. Silicon-on-Insulator, semiconductor membranes), plasmonic waveguides (e.g. metal nano-particle arrays, metal layers), also called Photonic Lightwave circuits (PLC). According to particular embodiments, the sensing systems could be implemented in a silicon-on-insulator platform. The high refractive index contrast allows photonic waveguides and waveguide components with submicron dimensions to guide, bend and control light on a very small scale so that various functions can be integrated on a chip. Moreover SOI offers a flexible platform for integration of resonator rings which in turn allows for even higher levels of miniaturisation. Using Silicon-on-insulator also has some technological advantages. Due to the CMOS industry, silicon technology has reached a level of maturity that outperforms any other plane chip manufacturing technique by several orders of magnitude in terms of performance, reproducibility and throughput. Nano-photonic ICs can be fabricated with wafer scale-processes, which means that a wafer can contain a high amount of photonic integrated circuits. Combined with the commercial availability of large wafers at a relative moderate cost, this means that the price per photonic integrated circuit can be very low.

In some particular embodiments of the present invention the channel 101 is curved such that the open end 102 of the channel 101 is in close proximity with the closed end 103 of the channel. The latter has the advantage that local background variations will more likely have the same effect on both ends of the channel as their position is more close to each other.

In one particular embodiment, the sensing system may be an implantable spectrometer for detecting small variations, e.g. in glucose concentration. The implantable spectrometer comprises a system 100 for measuring the concentration of a component in a liquid, whereby the measurement sensor 104 and the reference sensor 105 are sensitive for the component to be sensed, in the present example for glucose variations in the liquid. To measure small variations in the concentration of a component (e.g. glucose) in a liquid (e.g. blood) with high signal to noise ratio compensation with the reference signal as obtained in embodiments of the present invention is used. This allows to compensate for drifts in the measurement signal 205 picked up by the measurement sensor 104. In one particular example, the sensing system is implemented as a dualbeam spectrometer, wherein the light of one light source is split in two paths, a signal path and a reference path. In the exemplary embodiment given, the reference sensor 105 senses the same bodily fluids as the first sensor 104, except for the dynamically changing glucose concentration. Since the diffusion of the glucose molecules is slower than the change rate of the concentration, the concentration change is not measured by the second sensor. It is an advantage of embodiments of the present invention that filtering is not required. In certain situations filtering would not be an option as it is for example not possible to use a membrane for filtering glucose molecules because the glucose molecules are very small. It is an advantage of embodiments of the present invention that a reference signal can be created taking into account all variations in the human body present at the first sensor 104 except for the variations which are so fast that the diffusion time towards the closed end 103 prevents them from being detected at the closed end (e.g. the glucose concentration changes). In embodiments of the present invention the implantable spectrometer is implanted in living tissue.

Figure 3:
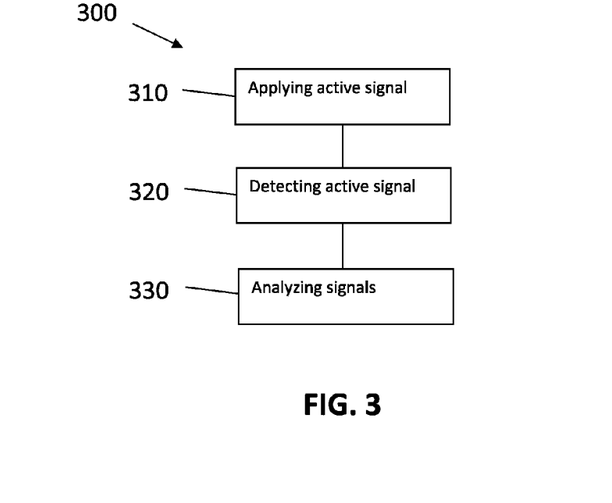
FIG. 3 illustrates an exemplary method for measuring the concentration of a component in a liquid in accordance with embodiments of the present invention.

In a second aspect the present invention relates to a method for sensing a component in a liquid. Such sensing may comprise determining presence and/or a concentration of the component in a liquid. The method comprises obtaining a measurement signal of a fluid to be characterized using a measurement sensor adjacent a first, open end of a microfluidic channel and obtaining a reference signal for the fluid to be characterized using a reference sensor adjacent a second, closed end of the microfluidic channel. The method further comprises compensating the measurement signal with the reference signal so as to filter out background influences. The method may be especially suitable for use with a system as described in the first aspect. By way of illustration, a schematic overview of an exemplary method according to the present aspect is shown in FIG. 3. The first step 310 in the method 300 is to provide a sample to the detector. The sample may be provided such that the fluid comes into contact with the first sensor at the open end 102 of the channel 101 and, through slow diffusion, with the reference sensor at the closed end 103 of the channel 101. In a next step 320 presence and/or concentration of the component in the fluid is sensed at the open end and at the closed end. If present, the presence and/or concentration of the component in the sample is sensed at the open end 102 of the channel 101 and for comparison, the fluid is sensed at the closed end 103 of the channel 101. In the next step 330 the difference between the received signal 205 at the open end 102 and the received signal 206 at the closed end 103 is analyzed in order to determine a component concentration in the liquid. Other standard or optional steps such as performing other data processing steps also may be included in a method according to an embodiment of the present invention, as will be understood by the person skilled in the art.

In a third aspect, embodiments of the present invention also relate to the use of a sensing system as described in the first aspect as a glucose sensor for diabetes patients.

By way of illustration, experimental results as obtained using systems according to the present invention are now discussed in more detail. The particular example refers to in vivo detection of glucose, although embodiments of the present invention are not limited thereto.

Figure 12:
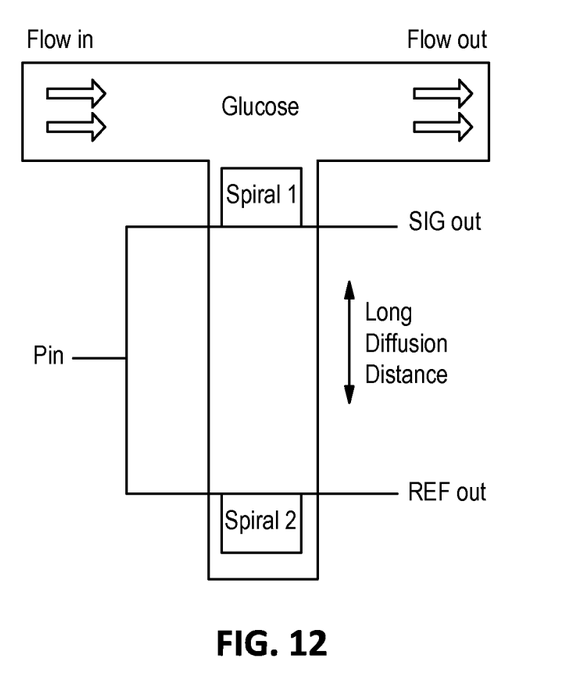
FIG. 12 is a schematic view showing principles for glucose detection.
Figure 13:
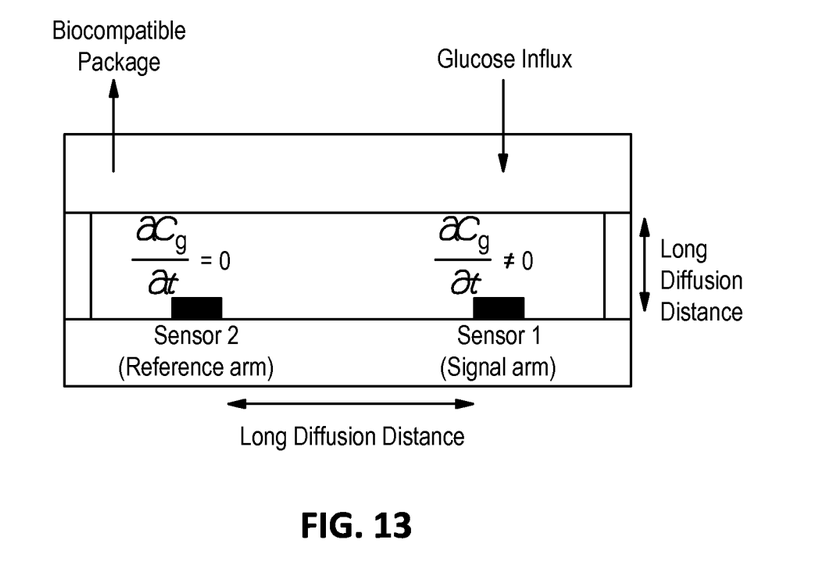
FIG. 13 is a schematic view showing implementation of a diffusion-delayed dual-beam evanescent sensor.

The 'source' of the glucose that one wants to detect is the glucose influx from the interstitial fluid into the implantable continuous glucose monitor. Measurements in the present example are obtained using the system as schematically illustrated in FIG. 2, using the principles as schematically illustrated in FIGS. 12 and 13. The measurement sensor is located close to this source and will experience all the fast variations that occur in the glucose concentration. This sensor thus serves as the signal, but is also sensitive to e.g. variations in body temperature and absorption of the interstitial fluid. The reference sensor, that serves as a reference, is located at a distance far from the source of glucose. The glucose molecules can only reach this position by the process of diffusion. Because the daily average glucose concentration is more or less constant the distance of the reference sensor was chosen as such that the glucose molecules need a day to reach the reference sensor. Given the diffusion coefficient of glucose in water (6.75e-9 cm^2/s) this distance is about 1 cm. The glucose concentration that is measured at the reference sensor is, thanks to the process of diffusion, the daily time-averaged value of the glucose concentration at the source. The reference sensor is, however, also sensitive to the same environmental situation as the signal sensor. Therefore, taking the ratio of the signal over reference arm measurements, yields the fast glucose variations while cancelling the common fluctuations. The results discussed are based on an implementation of a diffusion-delayed dual-beam evanescent sensor as schematically shown in FIG. 13.

It targets the detection of glucose in physiologically relevant concentrations. The evanescent sensor is integrated on a silicon-on-insulator (SOI) chip. The glucose sensor that we use is an integrated silicon waveguide that is routed into a spiral to minimize the sensor footprint. The evanescent tail of the transverse electric (TE) optical waveguide mode is used to interact with the sample fluid that surrounds the spiral waveguide. As the TE mode propagates through the waveguide, it is attenuated due to glucose according to the law of Beer-Lambert:

$$A = -\log(T) = \epsilon \cdot c \cdot L \cdot \Gamma.$$

in which T is the transmission, $\epsilon$ the absorptivity of glucose, c the concentration, L the length of the spiral waveguide and $\Gamma$ the confinement factor of the waveguide mode. The absorptivity is a function of the transmitted wavelength and serves as a unique fingerprint for glucose molecules. Thus, by measuring the transmission at different wavelengths the glucose concentration can be measured. The SOI chip is combined with micro-fluidics in poly-dimethylsiloxane (PDMS). The micro-fluidics has one flow channel and one perpendicular diffusion channel. The flow channel is used to apply glucose to the entrance of the diffusion channel. The signal spiral is located at this entrance. When glucose is present, the transmission through the spiral will decrease. The reference spiral is located at the end of the diffusion channel. The distance between signal and reference waveguide is approximately 1 cm. It takes glucose molecules about one day to move this distance by diffusion. While continuously measuring the transmission spectra of both signal and reference we apply different concentrations of glucose alternated with water.

Figure 4:
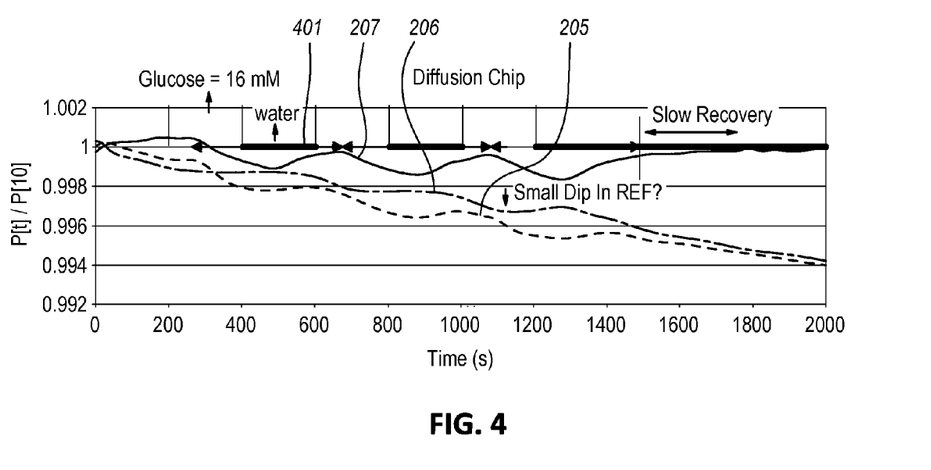
FIG. 4 shows a graph including the applied and measured glucose concentration measured in accordance with embodiments of the present invention.

During the experiment alternatingly a liquid with a glucose concentration of 16 mM (millimolar) and water are in contact with the open end 102 of the channel 101. This is illustrated by curve 401 in the graph of FIG. 4. The x-axis in the graph of FIG. 4 indicates the time axis, expressed in seconds. The y-axis shows the normalized signal with regard to the first measurement which is a measurement when water is in contact with the open end 102 of the channel 101, and this for the measurement signal 205, the reference signal 206 and the calibrated effect 207. Inspection of the measurement signal 205 in FIG. 4 shows the relationship with the glucose concentration. It also shows a drift in the measurement signal 205 over time. For accurate glucose concentration measurements it is important that this drift can be compensated for. As illustrated in FIG. 4 this drift is also present in the reference signal 206. The variation in glucose concentration is far less visible, indicating the concentration variation has indeed been averaged out. Therefore, by dividing the measurement signal 205 by the reference signal 206, the drift can be effectively removed as is illustrated in FIG. 4 by the calibrated effect 207.

Figure 5:
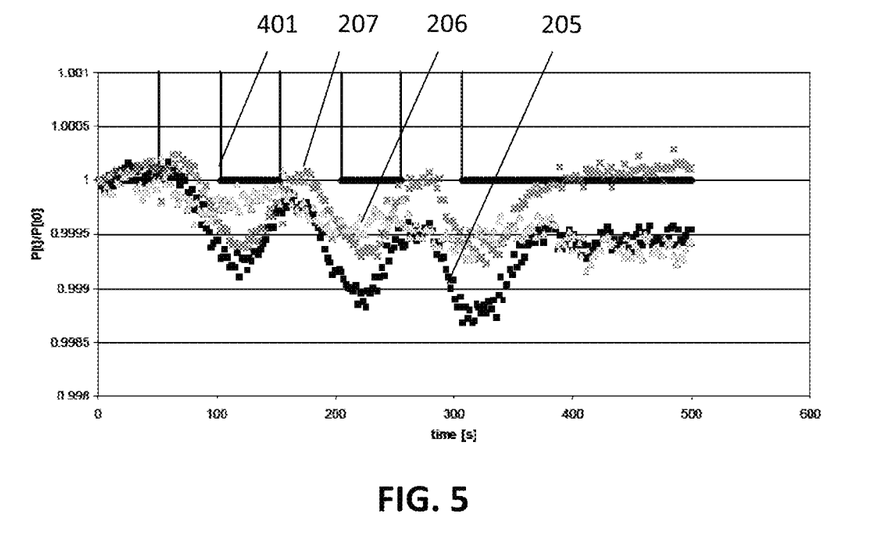
FIG. 5 shows a similar graph as FIG. 4 except for the pump rate which is higher.

The graph in FIG. 5 illustrates the results of a similar experiment but in this case at higher frequencies. Similar results can be seen.

Measurements also were performed spectrally.

Figure 6:
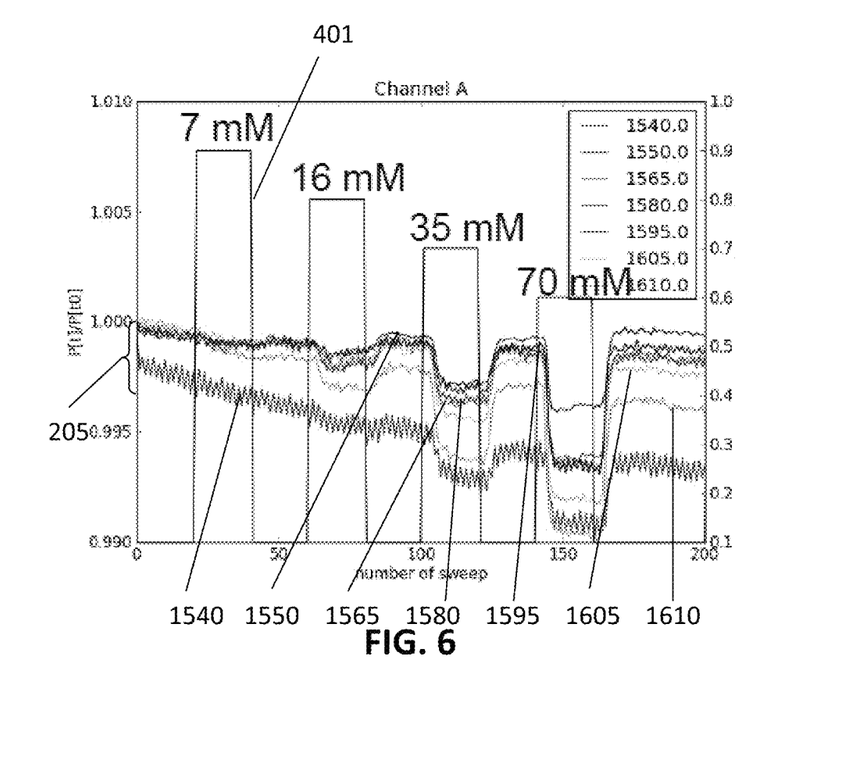
FIG. 6 shows the measurement signal in function of the sweep number and this for different applied wavelengths in accordance with embodiments of the current invention.
Figure 7:
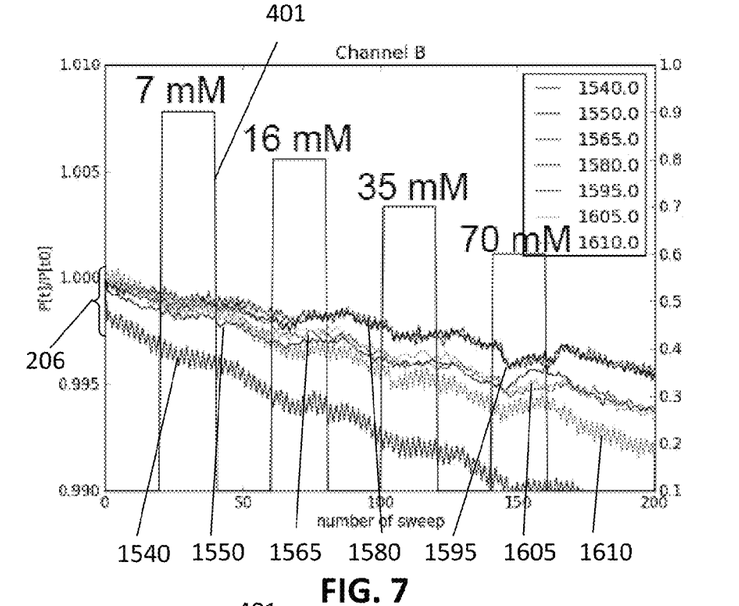
FIG. 7 shows the reference signal in function of the sweep number and this for different applied wavelengths in accordance with embodiments of the current invention.
Figure 8:
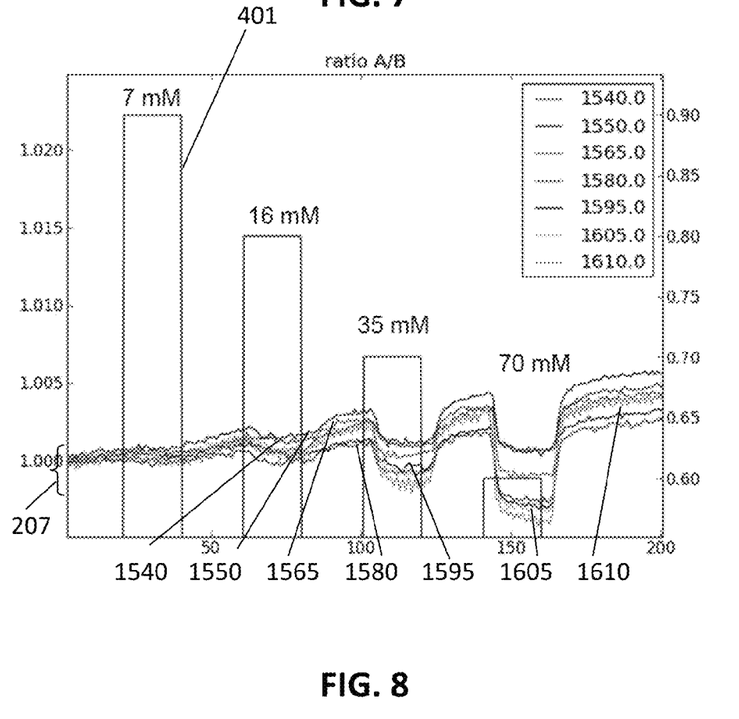
FIG. 8 shows the measurement signal divided by the reference signal in accordance with embodiments of the current invention.

FIG. 6 illustrates the effect the glucose concentration has on the measurement signal 205 and this for different wavelengths of the measurement signal 205. The effect is increasing with an increasing glucose concentration. The y-axis is normalized with regard to the first measurement. The x-axis represents the sweep number. During one sweep, a detector reading for wavelengths in the wavelength range is acquired. The effective glucose concentration 401 is also added to the graph in FIG. 6. FIG. 7 illustrates the reference signal 206 in function of the applied glucose concentration. The result is shown for different wavelengths of the reference signal. The drift of the reference signal is substantially the same as the drift in the measurement signal 205 shown in FIG. 6. Therefore the reference signal 206 can be used to calibrate out the drift in the measurement signal 205. This is illustrated in FIG. 8 showing the calibrated effect 207 for the different wavelengths. The calibrated effect 207 is in this case realized by dividing the measurement signal 205 by the reference signal 206.

Figure 9:
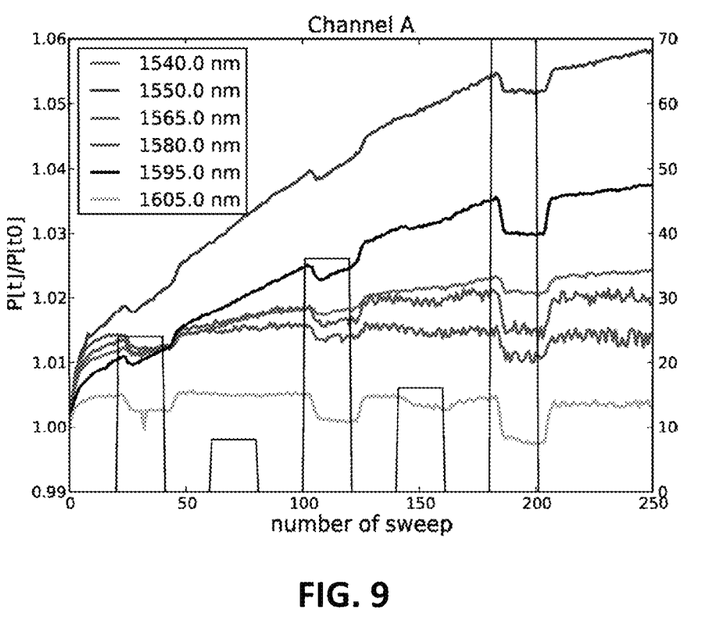
FIG. 9 to FIG. 11 illustrate respectively a measured signal, a reference signal and a ratio of both signals for a sensing of glucoses using a method according to an embodiment of the present invention.
Figure 10:
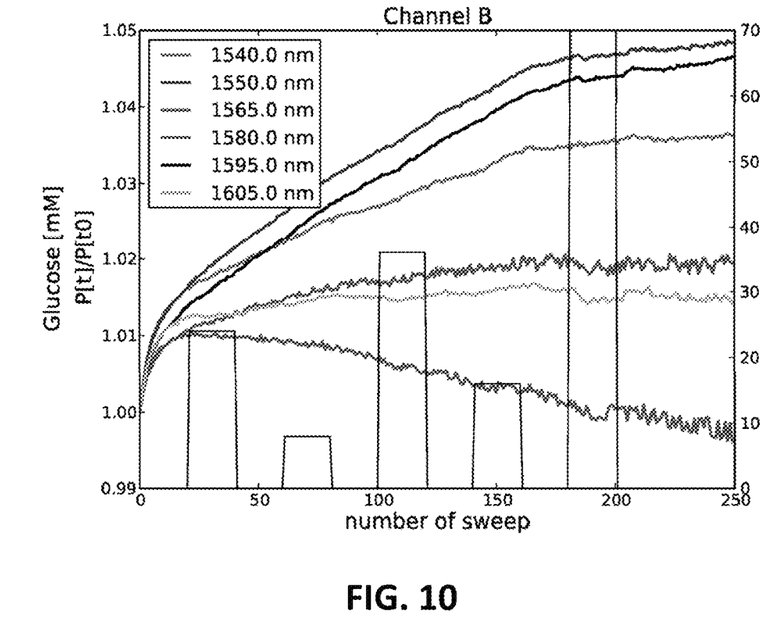
Figure 11:
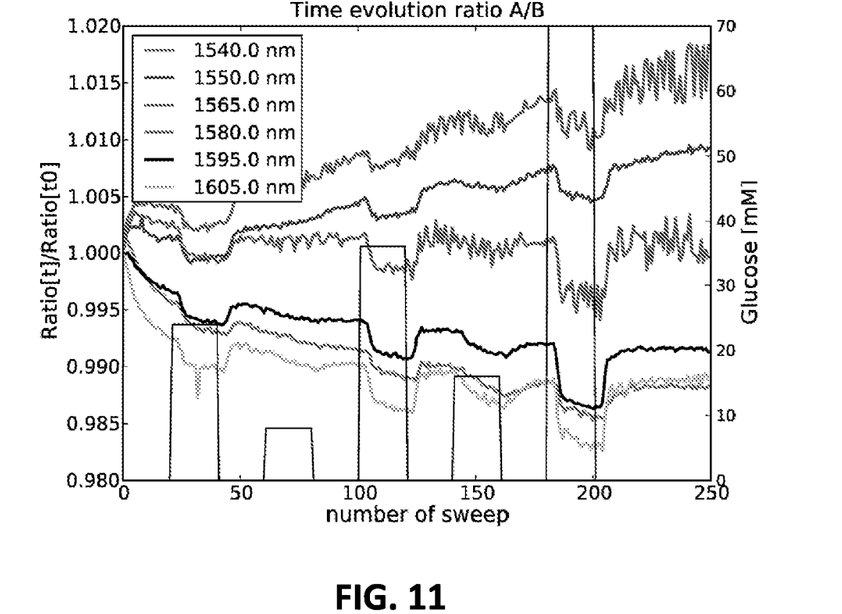

FIG. 9 to FIG. 11 illustrates results of a similar experiments, wherein FIG. 9 illustrates the measured signal measured, FIG. 10 illustrates the reference signal measured, and FIG. 11 illustrates the ratio of both signals. Both measurement signal and reference signal show wavelength dependent slow drift but it is clear that the signal arm shows good correlation with the applied glucose. The only changes in the reference arm are caused by a short (300 μm) common waveguide path that is in contact with glucose. The ratio shows a smaller slow drift and a clear correlation with the applied glucose concentration indicating that at least part of the background variation has been compensated for.

The invention claimed is:

1. A sensing system for sensing a component in a liquid, the system comprising:
   a microfluidic diffusion channel, the microfluidic diffusion channel comprising an open end and a closed end, the microfluidic channel providing a diffusion path for the component in the liquid to be sensed,
   at least one measurement sensor positioned at the open end, the measurement sensor being arranged for detecting a measurement signal indicating a characteristic of a portion of the component at the open end of the diffusion channel,
   at least one reference sensor positioned in the microfluidic diffusion channel adjacent the closed end, the reference sensor being arranged for detecting a reference signal of the liquid, the diffusion channel and reference sensor being arranged such that the reference signal indicates a characteristic of a portion of the component arriving at the reference sensor by diffusion through the diffusion channel, the system being configured for combining the measurement signal and the reference signal so as to filter out background influences.

2. A sensing system according to claim 1, wherein the measurement sensor is positioned in the microfluidic diffusion channel adjacent the open end.

3. A sensing system according to claim 1, wherein the measurement sensor and the reference sensor are any of an absorption sensor, a chemical sensor, an electrical sensor or an optical sensor.

4. A sensing system according to claim 1, wherein the measurement sensor and the reference sensor are based on a transmitter/receiver architecture wherein the transmitter of the measurement sensor is shared with the transmitter of the reference sensor.

5. A sensing system according to claim 1, wherein the measurement sensor and the reference sensor are optical sensors using a common excitation source as transmitter.

6. A sensing system according to claim 1, wherein the measurement sensor and the reference sensor are part of a dual beam optical sensor system.

7. A sensing system according to claim 1, wherein the measurement sensor and the reference sensor are spectral optical sensors allowing spectral characterisation of the fluid.

8. A sensing system according to claim 1, wherein the measurement sensor and the reference sensor are optical sensors based on a resonator element.

9. A sensing system according to claim 8, wherein the resonator element is an optical resonator ring.

10. A sensing system according to claim 1 wherein the measurement sensor comprises a first optical ring and wherein the reference sensor comprises a second optical ring and wherein the first optical ring is in contact with the liquid at the open end and the second optical ring is in contact with the liquid at the closed end.

11. A sensing system according to claim 1, wherein the microfluidic diffusion channel comprises a diffusion barrier for a component to be detected.

12. A sensing system according to claim 1, wherein the microfluidic diffusion channel has a curved shape such that the open end of the diffusion channel is nearby the closed end of the diffusion channel.

13. A sensing system according to claim 1, wherein the measurement sensor and the reference sensor are configured for directly combining the signals for compensating the measured signal with the reference signal.

14. A sensing system according to claim 1, the sensing system comprising a processor wherein the processor is configured to receive the measurement signal of the measurement sensor and the reference signal, and the processor is further configured to combine the measurement signal and the reference signal.

15. A sensing system according to claim 1, the sensing system being an implantable sensor for implantation into a living creature.

16. A sensing system according to claim 1, wherein the characteristic of the portion of the component at the open end of the diffusion channel is a presence of the component, a concentration of the component, an amount of the component, or a specific property of the component at the open end of the diffusion channel.

17. A sensing system according to claim 1, wherein the characteristic of the portion of the component at the closed end of the diffusion channel is a presence of the component, a concentration of the component, an amount of the component, or a specific property of the component at the closed end of the diffusion channel.

18. A sensing system according to claim 1, wherein the open end of the diffusion channel is open contact with an outer environment or volume in which the liquid is present, thereby the characteristic of the portion of the component at the open end of the diffusion channel changes at a faster rate than a rate of change of the characteristic of the portion of the component at the closed end of the diffusion channel.

19. A sensing system according to claim 1, wherein the length of the diffusion channel is at least two times a diffusion speed over time for the component in the liquid.

20. A method for sensing a component in a liquid, the method comprising:
obtaining a measurement signal of a fluid to be characterized using a measurement sensor positioned at an open end of a microfluidic diffusion channel, the measurement signal indicating a characteristic of a portion of the component at the open end of the diffusion channel,
obtaining a reference signal for the fluid to be characterized using a reference sensor positioned adjacent a closed end of the microfluidic diffusion channel, the microfluidic diffusion channel providing a diffusion path for the component in the liquid to be sensed, the diffusion channel and reference sensor being arranged such that the reference signal indicates a characteristic of a portion of the component arriving at the closed end by diffusion through the diffusion channel, and
compensating the measurement signal with the reference signal so as to filter out background influences.

* * * * *